(12) United States Patent
Sliwa

(10) Patent No.: US 8,444,579 B2
(45) Date of Patent: May 21, 2013

(54) SYSTEM FOR DELIVERING ACOUSTIC ENERGY IN CONNECTION WITH THERAPEUTIC ULTRASOUND SYSTEMS AND CATHETERS

(75) Inventor: John W. Sliwa, Los Altos Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1080 days.

(21) Appl. No.: 11/963,784

(22) Filed: Dec. 21, 2007

(65) Prior Publication Data

US 2009/0163836 A1   Jun. 25, 2009

(51) Int. Cl.
*A61B 8/00* (2006.01)
(52) U.S. Cl.
USPC .............. 601/2; 600/459; 606/31; 604/20; 604/21; 604/22

(58) Field of Classification Search
USPC . 600/459, 462, 471, 439; 606/31; 604/20–22; 73/623; 367/190
See application file for complete search history.

(56) References Cited

U.S. PATENT DOCUMENTS

| | | | |
|---|---|---|---|
| 5,368,557 A * | 11/1994 | Nita et al. | 604/22 |
| 6,267,734 B1 * | 7/2001 | Ishibashi et al. | 601/2 |
| 6,551,337 B1 | 4/2003 | Rabiner et al. | |
| 6,590,830 B1 * | 7/2003 | Garlick et al. | 367/8 |
| 6,660,013 B2 | 12/2003 | Rabiner et al. | |
| 6,685,657 B2 | 2/2004 | Jones | |
| 6,733,451 B2 | 5/2004 | Rabiner et al. | |
| 6,866,670 B2 | 3/2005 | Rabiner et al. | |
| 2003/0229331 A1 | 12/2003 | Brisken et al. | |
| 2004/0204729 A1 | 10/2004 | Cimino | |
| 2005/0043756 A1 | 2/2005 | Lavelle et al. | |
| 2005/0154309 A1 * | 7/2005 | Etchells et al. | 600/459 |
| 2005/0187514 A1 | 8/2005 | Rabiner et al. | |
| 2005/0215942 A1 | 9/2005 | Abrahamson et al. | |
| 2006/0216275 A1 * | 9/2006 | Mon | 424/93.2 |
| 2007/0112296 A1 | 5/2007 | Wilson et al. | |
| 2007/0161945 A1 | 7/2007 | Nita et al. | |
| 2007/0225619 A1 | 9/2007 | Rabiner et al. | |
| 2007/0239011 A1 * | 10/2007 | Lau et al. | 600/439 |
| 2007/0270447 A1 | 11/2007 | Hunter et al. | |

OTHER PUBLICATIONS

International Search Report and Written Opinion for PCT/US2008/86558 mailed Feb. 10, 2009.
OmniSonics—Developing Medical Devices Utilizing OmniWave Technology, OmniSonics Medical Technologies, Inc., 2003.

* cited by examiner

*Primary Examiner* — Parikha Mehta
(74) *Attorney, Agent, or Firm* — Dykema Gossett PLLC

(57) ABSTRACT

The invention discloses a system for delivering acoustic energy to a subject in connection with high intensity focused ultrasound (HIFU) systems. In an embodiment, the system comprises an optionally disposable waveguide-attached ablation applicator coupled with an optionally re-usable waveguide, and an optional acoustic power source. The systems may comprise acoustic energy exit port intensity control, waveguide heat-sinking, and transducer operational adjustments that accommodate waveguide effects on the traversing acoustic power.

32 Claims, 4 Drawing Sheets

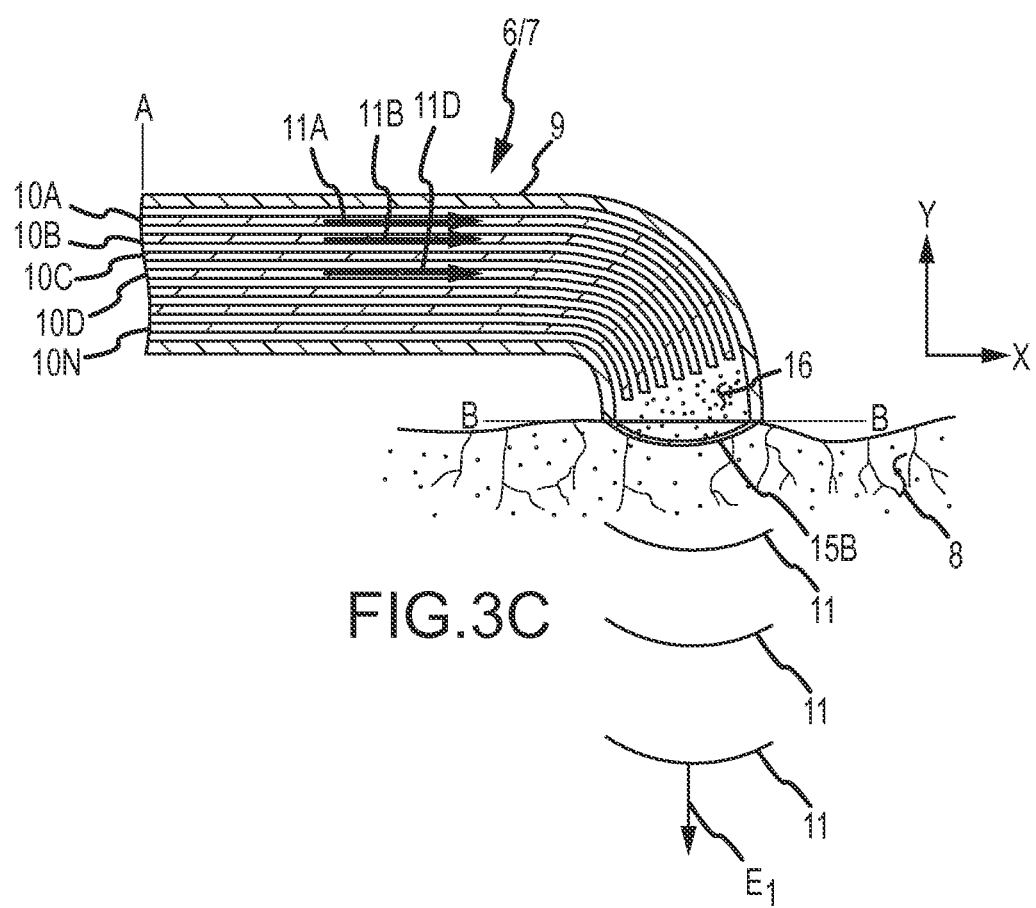

SYSTEM FOR DELIVERING ACOUSTIC ENERGY IN CONNECTION WITH THERAPEUTIC ULTRASOUND SYSTEMS AND CATHETERS

CROSS-REFERENCE TO RELATED APPLICATIONS

None.

BACKGROUND OF THE INVENTION a. Field of the Invention

The instant invention is directed to therapeutic ultrasound systems, such as surgical HIFU ablators, comprising acoustic energy waveguides and acoustic energy-guiding applicators for imparting the acoustic ablative energy to, into or upon target tissues. The instant invention allows for inexpensive if not disposable energy applicators which connect to a nondisposable energy waveguide which in turn connects to an energy providing console.

b. Background Art

Catheters have been in use for medical procedures for many years. Catheters may be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" uses a catheter to apply localized radiofrequency (RF) heating to a selected location within the human body to create thermal tissue necrosis.

In a normal heart, contraction and relaxation of the heart muscle (myocardium) takes place in an organized fashion as electrochemical signals pass sequentially through the myocardium from the sinoatrial (SA) node located in the right atrium to the atrioventricular (AV) node and then along a well defined route which includes the His-Purkinje system into the left and right ventricles. Sometimes abnormal rhythms occur in the atrium which are referred to as atrial arrhythmia. Three of the most common arrhythmia are: (1) ectopic atrial tachycardia, (2) atrial fibrillation, and (3) atrial flutter. Arrhythmia can result in significant patient discomfort and even death because of a number of associated problems, including: (1) an irregular heart rate, which causes a patient discomfort and anxiety; (2) loss of synchronous atrioventricular contractions which compromises cardiac hemodynamics resulting in varying levels of congestive heart failure; and (3) blood flow stasis, which increases the vulnerability to thromboembolism. It is sometimes difficult to isolate a specific pathological cause for the arrhythmia, although it is believed that the principal mechanism is one or a multitude of stray electrochemical circuits within the left and/or right atrium. These circuits or stray electrical signals are believed to interfere with the normal electrochemical signals passing from the SA node to the AV node and into the ventricles. Efforts to alleviate these problems in the past have included administering various drugs. In some circumstances, drug therapy is ineffective or wears off and frequently is plagued with side effects, such as dizziness, nausea, vision problems, and other difficulties.

An increasingly common medical procedure for the treatment of certain types of cardiac arrhythmia and atrial arrhythmia involves thermal ablation of heart tissue to cut off the path for stray or improper electrical signals. Such procedures may be performed by thermal ablation catheters. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the thermal ablation procedure in the heart. RF ablation catheters produce thermal lesions and electrically isolate or render the targeted tissue non-contractile at particular points in the cardiac tissue by physical contact of the cardiac tissue with an RF electrode on the ablation catheter and application of RF energy through the RF electrode. The thermal lesion partially or completely blocks the stray electrical signals to lessen or eliminate arrhythmia.

Thermal ablation procedures, however, may be used to treat a variety of other conditions, not just atrial fibrillation. These conditions include liver and kidney disease, and cancer. Many more applications of thermal ablation procedures in the areas of reproductive health, the urinary tract, cosmetic surgeries, dermatology and neurology are currently being developed. Some of these, rather than employing a catheter, employ one or more minimally invasive RF needles or penetrating electrodes/antennas which is/are surgically inserted into the cancer tumor for example.

High-Intensity-Focused-Ultrasound (HIFU) is increasingly being used for performing lesion-making thermally ablative surgeries. With HIFU energy, physicians can create very precise, consistent, and effective thermally ablative lesions without stopping the patient's heart. In this already productized and available procedure, energy is applied to the outside of a beating heart epicardially. By adjusting acoustic power and wavelength, the acoustical energy is focused to ablate precise areas of cardiac tissue without impacting surrounding tissue or blood vessels, effectively creating continuous full-thickness lesions. An advantage of HIFU is that it is comparatively minimally invasive in that at-depth tissues can be lesioned from a nearby tissue or organ surface.

In HIFU, acoustic waves propagate through the tissue, and a portion of that wave energy determined by the tissue acoustic-attenuation is absorbed by the tissue and converted to heat. With the acoustic wave focused into beams, a very small acoustic focus may be achieved deep in tissue and the heat developed at that focus concentrated. If hot enough (65° to 85° C.), the tissue thermally coagulates in less than a second, wherein proteins denature and thermal ablation (tissue necrosis) occurs. At even lower temperatures of 45-65 degrees C., necrosis in tissue occurs in seconds, the hotter the faster. By focusing at more than one place or by scanning the focus, all of a target volume may be thermally ablated to a focal temperature.

Surgical ablation is often performed on patients already receiving cardiac valve replacement or repair, or coronary artery bypass, due to the fact that a surgeon already has access to the patient's heart and the above medical issue has caused AF to develop as a consequence. As HIFU surgical ablation enables less invasive procedures, increasing numbers of patients are becoming eligible for this as a standalone procedure.

A strategy wherein at least the acoustics-producing portions of an acoustic or HIFU surgical ablator device would be off-board the handheld ablator portion would allow for a disposable ablator applicator and a separately packaged acoustics-producing transducer in the console. This means that the applicator can be very inexpensive as it does not produce the acoustics; it just directs acoustics. Most existing acoustic ablators are handheld transducers which make their own acoustics with energy from an attached power cord. This makes them expensive-regardless of whether they can be reused or not.

Because most existing handheld ablators contain ultrasonic transducers, they are expensive to dispose of. If one reuses them, as is often the case, their lifetime and reliability will then be impacted by their repeated sterilization between patients.

What would be highly attractive is a disposable HIFU applicator which receives offboard acoustical energy from an attached console. Such an applicator would be connected to an acoustic energy waveguide, the purpose of which is to carry or transmit the acoustic energy from the console to the disposable applicator.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention provides systems for delivering acoustic energy to a subject, and methods of using the same, wherein the systems comprise a transducer; a means to power the transducer to emit acoustic energy; a connecting delivery waveguide that includes an input port, an exit port, and a power detection sensor positioned at or near the exit port of the waveguide and operably connected to the transducer; and an acoustic energy applicator in acoustic communication with the subject, wherein the emitted acoustic energy passes through the waveguide to the applicator, and the power detection sensor provides feedback to the transducer, such that if the exit power decreases from a selected exit port power, the input port power is increased to maintain the selected exit port power. The waveguide may further comprise a filler or acoustic propagation material or medium, wherein the filler or propagation material may be a liquid, gel, paste, cream, emulsion, water or aqueous solution, or combinations thereof. An example of a suitable aqueous filler material is saline. The filler material may also be at least one metallic, glass or ceramic fiber, wire or cable that runs along the waveguide and along which acoustic energy is propagated. The waveguide can further comprise a wall material that is porous, permeable, acoustically reflective, gaseous, vapor-containing, air-saturated or air-infiltrated. In some embodiments, the waveguide wall comprises a porous, air-filled polymer. The filler material can be at least partially enclosed inside the waveguide, wherein the filler material does not substantially infiltrate the wall material during acoustic power propagation along the waveguide. In some embodiments, the interior of the waveguide comprises low-loss wires or fluid and the surrounding waveguide shell or outer wall is formed of high-loss air or vapor wherein the vapor comprises the reflective waveguide wall. A vacuum may also be provided in the waveguide wall to de-gas the waveguide core acoustic propagation medium such as to degas saline. The acoustics-generation transducer typically includes a face across which emits energy into the waveguide and preferably allows for area-wise phase-delay control across the transducer emission face. An example of this would be a phased array transducer comprised of a square of M×M sub-elements. In some embodiments, the transducer is capable of an area-wise variation in at least one operational acoustic parameter, the variation being used to deliver power through the waveguide or to prevent degradation of acoustic power losses in said waveguide such as by correcting for phase variations due to waveguide bending or due to the irregular internal geometry of an applicator. The transducer can comprise a multi-element or multi-segment transducer, wherein, for example, an operational parameter such as a phase delay from firing of the transducer element is varied between at least two of the elements or segments. Operational parameters may include amplitude, phase, frequency, or excitation waveform. The power detection sensor may be used for feedback to the user to infer the power being successfully propagated to a point anywhere along the acoustic propagation path, including that delivered to a subject. The acoustic power detection component might also be located in the waveguide-removable therapy applicator. This would also account for at least some acoustic losses caused by the applicator itself or the connection thereof to the waveguide.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 3A-C depict some disposable applicator embodiments.

DETAILED DESCRIPTION OF THE INVENTION

Figure 1:
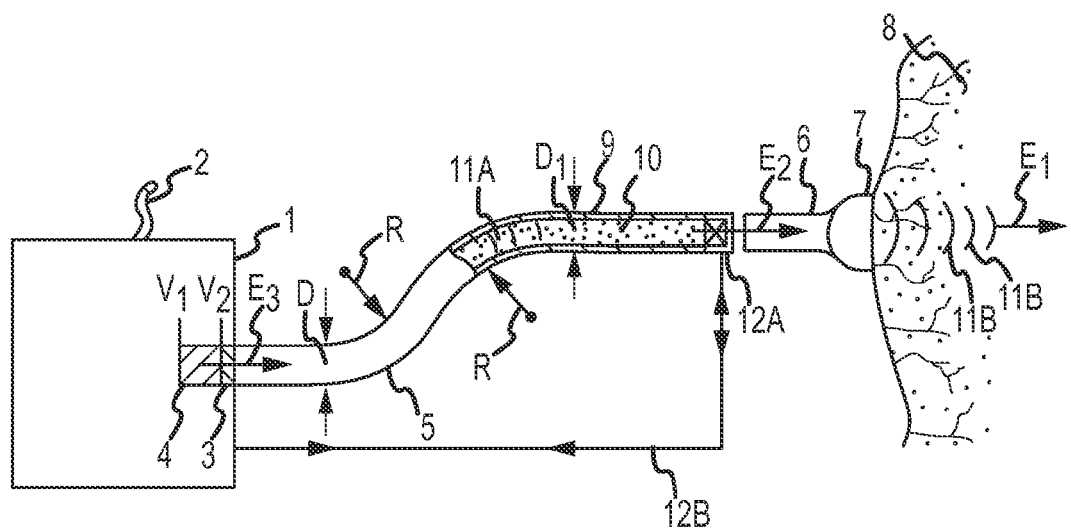
FIG. 1 shows a schematic of a HIFU system according to an embodiment of the invention, and highlights an exit-port power sensor and a flowed and cooled waveguide.

The present invention provides HIFU and other therapeutic ultrasound systems, such as surgical ablators, comprising a source of acoustic energy, a waveguide that guides the acoustic energy to an applicator, and an applicator that is in acoustic or physical contact with tissue in or under which an ablative lesion is to be formed. The invention provides waveguide-attached ablation applicators that are preferably and affordably disposable while re-using the waveguide and the acoustic power sources, thus maximizing cost savings and maintaining safety. Most likely the acoustic power source would be mounted in a console or control box and have the acoustic waveguide plugged into it. Note that a disposable applicator eliminates a sterilization procedure. During a therapeutic or ablating procedure the user may elect to wrap the waveguide, if not also portions of the applicator, in a disposable sheath.

HIFU waveguides can theoretically present severe thermal and power-density control issues, particularly if the waveguides require flexure, which bends and kinks reduce the efficiency of acoustic wave propagation and cause unwanted damaging heating at the kink or bend. The present invention can, among other things, address such problems in practical and cost effective ways. Three aspects associated with embodiments of the invention can compensate for the efficiency-loss and resultant undesirable self-heating issues potentially associated with flexible high power acoustic waveguides:

(1) Exit Port Intensity Control: Waveguide flexure can cause substantial variations in power transmission and can cause hotspots to develop within the waveguide such as at bends. The present invention can address the power control problem by including a power-detection sensor at or near the waveguide exit-port region or in therapeutic applicator that provides feedback to the acoustics-producing means. In this manner, if the exit power drops due to bending or distortion, the system applies more input-port power to maintain a select or predetermined exit-port power.

(2) Heat-Sinking of the Waveguide: Another concern is waveguide over-heating-both globally and locally, particularly when bending occurs or when the above corrective power is applied to compensate for bends or other losses. To solve this issue the waveguide may be cooled and/or may be provided with a heatsink; for example, by using active cooling. In one embodiment, the HIFU waveguide comprises a water-core waveguide, wherein flowing water or other aqueous solution—the water, saline or other aqueous solution-is the waveguide coolant as well as the acoustic propagation medium. The coolant may be recirculated or otherwise dispersed or disposed of In one embodiment, the liquid coolant is encased within a porous air-filled liner jacket that comprises porous air-filled TEFLON® that has not surprisingly air-like acoustic properties. Further, the porous air-filled liner jacket can support a vacuum across its thickness that may be used to de-gas the coolant. Any gas or a vacuum will act as the desired acoustic reflector needed on the waveguide walls.

(3) Transducer operational adjustments to accommodate waveguide effects and other phase aberrations: Optionally, a transducer that generates acoustic waves may be included in an embodiment of the HIFU system which provides for phase-delay control across the transducer face in any pattern. The face of the transducer emits into the mouth cross-section or core of the waveguide. The user or automatic circuitry can vary the phase-delay and/or amplitude of the various sub-elements of the emitting transducer to negate at least a portion of undesired waveguide phase distortions and amplitude non-uniformities. The exit-port control above can provide feedback for such manipulations. Because acoustic energy is being targeted to a distant source through a waveguide, lost energy may be compensated by using more powerful transducers provided the waveguide can be sufficiently cooled.

Thus the various embodiments of the invention comprises three or more aspects that may be used singly or in combination to overcome previous limitations: (1) sensors that monitor delivered acoustic power; (2) cooling and isothermalization to negate power inefficiencies/loss; and (3) transducer operational adjustments to negate acoustic power distortions that effectively "pre-distort" the power beam so that the therapeutic beam being delivered to the patient is what is desired.

The present invention and various embodiments are now discussed in view of the Figures. Of course, one of skill in the art will appreciate that many changes to these embodiments may be made that do not depart from the scope and spirit of the present invention.

FIG. 1 shows an embodiment of a HIFU system according to an embodiment of the invention. This embodiment comprises a control console or system box 1 having a power-cord 2. An ultrasound transducer that includes a piezocrystal 4 and preferably an overlying acoustic matching layer 3 are depicted having electrodes that electrically-pulse the crystal with a voltage difference or time-varying continuous waveform V1-V2 in a known manner. The transducer 3, 4 is shown emitting acoustic energy $E_3$ rightward into a coupled acoustic waveguide 5, which may be advantageously made of a flexible material. While FIG. 1 shows just one embodiment of a transducer, any acoustics-producing energy source including piezoceramic, electrostatic and magnetostrictive known types may be used to provide acoustic energy.

Acoustic waveguide 5 can have a generally tubular extended shape, and, as illustrated in FIG. 1, has a round cross-section. The shape of the waveguide 5, however, may be rectangular or elliptical; the waveguide 5 can vary in its diameter along its length, or even have one or more sections that are rotated such that the waveguide 5 is spiral shaped. A round shape has the advantage of not having "favorite" bending planes requiring waveguide twisting. Generally, the waveguide 5 may be 1 to 7 feet long, preferably 2 to 6 feet. The waveguide 5 of FIG. 1 is shown having two bends in it of radius R, but the number of bends may be fewer or more, depending on the particular application. In any case, acoustic energy of the type $E_3$ may be seen inside the waveguide 5 as rightward moving acoustic waveforms of the type 11A moving at the speed of sound in the core liquid. Waveguide 5 has an outside diameter D. Waveguide 5 comprises a wall material(s) 9 and a filler or acoustic propagation medium(s) 10. The filler material 10 shown may be aqueous, such as saline, and more preferably, sterile saline. The filler material 10 may be, for example, a flowable material, such as saline, as well as solid fillers, gel fillers, or structured solid fillers, the latter comprising, for example, bundles of generally parallel acoustics-carrying glass or metal fibers. In any case the acoustic propagation medium will have low acoustic attenuative losses as does water, many other liquids and gels, most metals and glasses and fibers thereof The wall material 9 as shown in FIG. 1 may comprise, for example, expanded porous polymers, such as those of the porous TEFLON® family: polytetrafluoroethylene, perfluoroalkoxy, and fluorinated ethylene propylene; in one embodiment, the filler material 10 does not substantially infiltrate the wall material 9 during acoustic power propagation along the waveguide 5. If it did infiltrate the wall deeply the wall would not be as good of an acoustic reflector. The waveguide 5 is in acoustic communication with a treatment applicator 6 having a tissue-contacting head 7. Applicator 6 with tissue-contacting head 7 is shown contacting a target tissue 8 of a subject. The target tissue 8 may be any internal or external tissue of a subject. A subject may be a mammal or other animal. Specifically, the subject is preferably a human. As for normal transducers of the HIFU or imaging type, they may operate across a water gap into tissue, as water is an excellent acoustic conductor and acoustic window. However FIG. 1 depicts direct applicator/tissue contact.

As shown in FIG. 1, acoustic energy $E_3$ enters the waveguide 5, $E_2$ leaves the waveguide 5 and enters the applicator 6, resulting in acoustic energy El, which is the acoustic energy actually coupled with, and delivered to, the target tissue 8 and leaving from the applicator. Obviously, if the applicator has some of its own energy losses then $E_3$-$E_2$ may be somewhat bigger than $E_1$. In an embodiment, air-filled, gas filled or vacuum filled porous TEFLON®, may be used for the wall material 9 of the waveguide 5. For moderate vacuums the surface tension of the porous TEFLON® is high enough to forcefully expel and keep out the liquid. This preserves the acoustic reflectivity yet allows water degassing. Therefore, the filler material 10 contacts a combined flexible polymer/air reflective surface when a flowable filler material 10, such as saline, does not permeate the liner surface. In an embodiment, the size and spacing of the air-bubbles or cavities in the expanded porous polymer of the confining reflective wall 9 is of a size-magnitude smaller than the wavelength of propagating ultrasound energy such that they do not individually interact with the acoustic waves. In this manner the expanded porous polymer appears isotropically reflective to the passing acoustic radiation.

In an ideal system, no acoustic energy is lost or wasted as it leaves the transducer 3, 4 and travels into the target tissue 8. In reality, a waveguide 5 absorbs acoustic energy, which in effect may be compounded when waveguide 5 is bent. In such cases, acoustic energy $E_2$ may be significantly different and less than acoustic energy $E_3$. The difference is substantially accounted for by conversion of acoustic energy into thermal heat and phase integrity changes. Such conversion can, for example, be caused by acoustic interferences created by bending, and particularly bending that also distorts waveguide 5 cross-section and/or properties. Low power waveguide design is known in the art, which teaches that optimal waveguide cross-sectional dimensions may be derived knowing the acoustic wavelength, propagation medium and waveguide wall materials. So in summary, we can correct for power losses by driving the source transducer 3, 4 harder. We can correct for phase errors due to waveguide bending and path-length variations by utilizing a multielement transducer whose phase from element to element can be adjusted. Such phase errors will destroy constructive wave combination at the tissue and therefore effectively kill useful achieved power. The same multielement transducer can also phase correct for path-length differences introduced by an applicator 6. We include in our inventive scope the applicator 6 performing focusing and/or the transducer 3, 4 performing focusing in any manner. Note that applicator 6 could easily incorporate a low-profile Fresnel-type acoustic lens which focuses substantially plane-wave energy arriving there from the console. We also note that a flowed acoustic propagation liquid will create focusing-like phase delays because of the different velocities of the liquid as a function of radius from the center of the flowing core.

FIG. 1 also shows a power sensor 12A at a point at or adjacent to the coupling into the applicator 6. It might alternatively be located in the applicator 6, perhaps even close to the tissue. While FIG. 1 shows only one sensor 12A, multiple sensors may be used, and they may be located in closer proximity to the subject, as well as in, or on, the applicator 6 itself. Such a sensor might also be an area-wise sensor rather than a point sensor. The sensor 12A may communicate with the control console 1 via, for example, a feedback loop or connection 12B. A "power sensor" 12A is any sensor that either directly measures acoustic power or acoustic pressure, or measures a property, such as temperature, that may be correlated with acoustic power or pressure or from which acoustic power may be inferred. Using the power sensor 12A, control console 1 may be informed, for example, via feedback loop 12B, to adjust power for acoustic energy E3 such that power of acoustic energy E2 remains relatively constant. Alternatively, the input power for acoustic energy E3 does not need to be adjusted if power fluctuations are tolerable in terms of total treatment time and/or actual dose delivered. Alternatively, the operator can adjust treatment time in response to knowledge of acoustic power fluctuations. Because the principle task of the waveguide 5 is to efficiently deliver power to the applicator 6 and ultimately to the target tissue 8, to help negate power losses, power may be adjusted in an area-wise manner at the transducer 3, 4, by varying any one or more of power (amplitude), phase, frequency, etc. Area wise transducer 3, 4 corrections might be based on an area wise sensor 12a or, perhaps, on a single point sensor in a desired focal region of the beam.

If the sensor 12A is placed inside an applicator 6, variations in the ability of the applicator 6 itself to pass power into the target tissue 8 may be monitored and the acoustic energy E3 accordingly modulated by the operator or by the control console 1 automatically. Within the scope of the invention is the use of a sensor 12A at a number of locations, including at, or in, the target tissue 8, that provides the control console 1 with information used, directly or indirectly, for compensating for power variations. The principle is the correction of a variable delivery system to attain controlled and/or repeatable therapies. Again, we emphasize that undesirable power variations could be caused by waveguide bending, the shape of the applicator, or phase errors across the area of the waveguide core propagation medium.

Even with minimal acoustic power loss, the waveguide 5 can significantly heat due to the high power injection of HIFU transducers, such as by transducer 3, 4, particularly at bends or in connection with other structural distortions. Thus in another aspect of the invention, which may be used with the previously discussed aspects, is a means of removing heat from the waveguide 5.

FIG. 1 depicts a waveguide 5 having a wall material 9 and a filler material 10, wherein the filler material is flowable. Although not shown, one could easily flow a flowable filler material 10 along the length of the waveguide 5. Aqueous solutions can be used to transport heat effectively. They are also acoustically of low loss. Suitable aqueous solutions that may be used as flowable filler material 10 include water, isotonic saline, Ringer's solution, and phosphate buffer solutions.

By flowing the filler material 10, even at low flow rates, substantial heat can be transported out of the waveguide 5, both axially and radially, and can even ("smooth-out") hotspots in or on the waveguide 5. The system, as pertaining to the flowable filler material 10, may be a closed system, wherein the flowable filler material 10 is recirculated, or an open system, wherein the flowable filler material passes through the system and is either delivered to the target tissue 8, or otherwise dispersed or disposed. In that case a source of fresh and preferably room-temperature or 37 deg C. temperature water would be employed. Typically, for surgical applications, water being delivered to tissue will be between room temperature and 37 Deg C. The waveguide will heat the water to some degree and this can be taken into account.

In one embodiment, the control console 1 monitors acoustic power and provides waveguide 5 cooling. High acoustic power may be effectively delivered via the waveguide 5 to the target tissue 8, even if the acoustic power of E3 entering the waveguide input varies by 20-50% to deliver effective power to the tissue. In an embodiment, the control console 1 can adjust its output (or an operator can adjust the output) by 20-50% such that an output power of acoustic energy E2 or E1 remains substantially constant at sensor 12A. In this manner the shortest advisable therapy may be delivered.

In yet another embodiment of the invention, the system comprises a transducer 3, 4 that can apply area-wise waveform phase and/or amplitude corrections across its own emission surface at each transducer sub-element if desirable. As an example, transducer 3, 4 could be a disc-shaped transducer having pie-shaped or ring-shaped slices or segments, wherein each slice is separately drivable in terms of amplitude and/or phase. Phase distortions or attenuative amplitude losses occurring along the waveguide 5 may be at least in part negated by area-wise power, phase or frequency adjustments at the transducer 3, 4. The ability to do phase adjustments in an area-wise manner also allows for the system to provide a beam focusing action. In that scenario it might be arranged that the applicator need not focus itself for example.

Figure 2A:
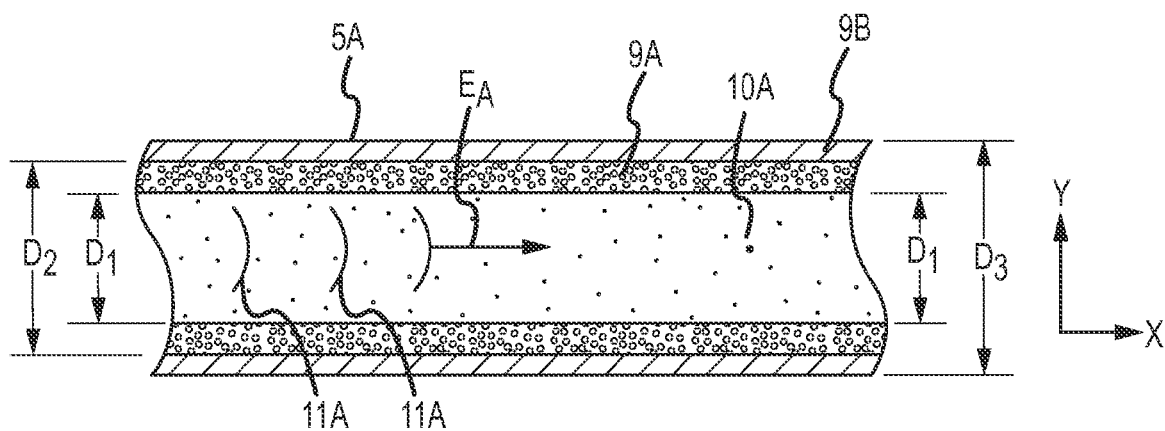
FIGS. 2A-C show different waveguide embodiments.
Figure 2B:
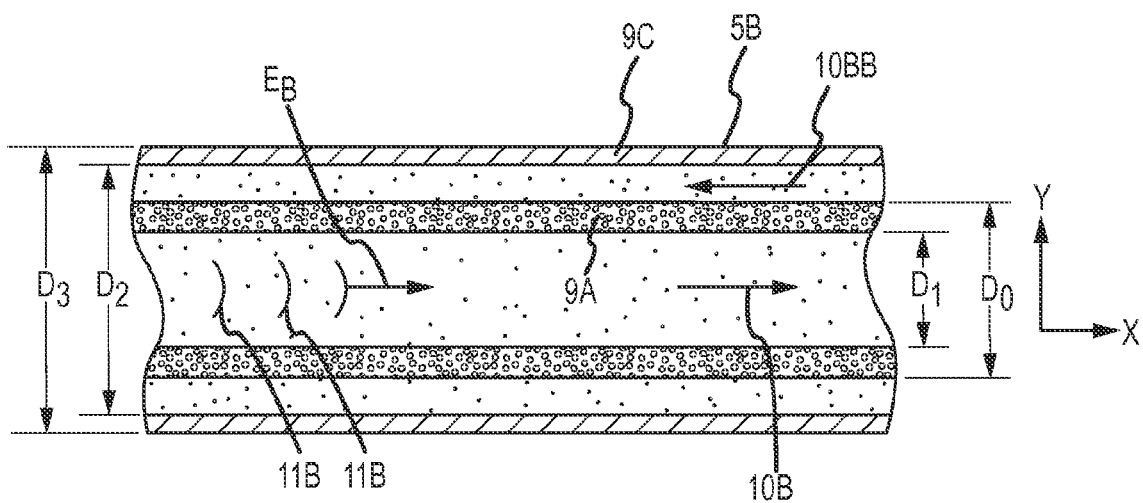
Figure 2C:
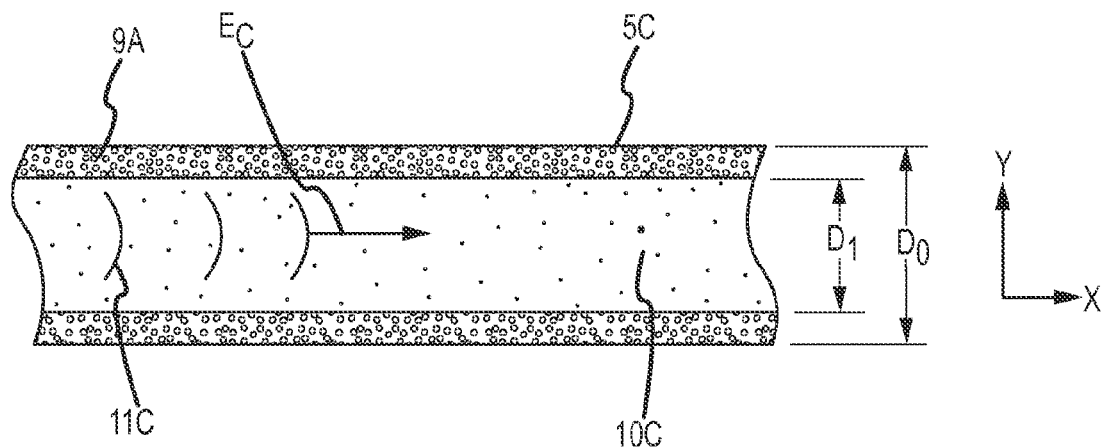

Further waveguide 5 embodiments are now illustrated in FIGS. 2A-2C. FIG. 2A shows a fluid-filled porous tube comprising an expanded air-filled porous polymer of the type shown in FIG. 1 that is modified to encompass an overcoating (encapsulating) material with a modification. Note that in FIG. 2A the expanded porous polymer tube material 9A is encapsulated with a jacket 9B. Thus the waveguide 5 has an outer diameter $D_3$, an outer expanded porous polymer diameter $D_2$, and an inner expanded porous polymer diameter $D_1$. It is the diameter $D_1$ that contains the propagating ultrasound energy. Jacket 9B material could be, for example, an extruded sleeve or a heat-shrunk skin of urethane or PVC. The jacket 9B may be used to: (a) keep the expanded porous polymer clean; (b) enhance distortion-resistance or buckling-prevention of the waveguide during bending; (c) enhance heat redistribution; (d) allow gaseous pressure-control in the expanded porous polymer such that the critical fluid-ingress pressure may be raised, or the fluid de-gassed by pulling a vacuum between diameters $D_1$ and $D_2$. The waveguide 5 can include braided or patterned wrappers, or woven over-layers known to one of skill in the art to enhance diametral and/or torsional rigidity. These can be incorporated in the overlayer 9B. Typically the waveguide 5 will be reusable so it will typically be designed to be wet-wiped with sterilant and utilized while wrapped in a disposable sheath (sheath not shown).

FIG. 2B shows a TEFLON® waveguide 5B situated inside another tube with a jacket 10BB encapsulating additional filler material. The waveguide 5B comprises an outer jacket 9C inside of which is an outer filler material jacket 10BB and a porous TEFLON® tube 9A. It will be noted that in FIG. 2B, two filler material compartments are shown, containing filler material 10BB and 10B. As for FIG. 1, filler material 10B, of FIG. 2B transports the ultrasound energy $E_B$. The embodiment shown in FIG. 2B provides recirculation of filler material 10B, 10BB that is flowable, such that the flowable filler material 10B, 10BB passes down waveguide 5 fluid-space and back up the outer filler material jacket. In this embodiment, ultrasound waves 11B travel down an unwettable, air-filled inner diameter $D_1$, functioning effectively as an acoustically reflective surface. The fluid return path is bounded by diameters $D_0$ and $D_2$. Appropriate spacers that maintain the jacket containing filler material 10BB gap-dimension without interfering substantially with flowable filler material 10B, 10BB flow can also be incorporated. A convenient shape for such spacers is in the form of a helix or coil. Such spacers, for example, may be helically wound spacer strips. If flowable filler material 10B, 10BB is being recirculated, the flowable filler material may not need to be physiologically compatible as it may not contact subject tissues depending on the specific design of the applicator and waveguide. Other useful flowable filler materials in closed systems may be, for example, fluorinated hydrocarbons, silicone liquids having boiling points and/or cavitation thresholds above that of water, or de-gassed water. Such a closed system will typically require a membrane at or near the applicator through which the acoustics leave the waveguide and enter the body. In this manner the applicator can be changed without draining the waveguide of fluid, a convenience but not a design requirement.

FIG. 2C shows yet another embodiment of a waveguide 5C useful in the systems of the present invention. Filler material 10C is a solid acoustic filler core-material; the compartment holding the filler material 10C is encapsulated by jacket 9A. Acoustic energy $E_C$ is depicted as waves 11C. Material of jacket 9A may be porous TEFLON®; however, its function is somewhat different than the embodiments shown in FIGS. 2A-B. In FIG. 2C, the main purpose of the porous TEFLON® coating is to prevent significant acoustic energy leakage into objects (or the operator's fingers) that touch the outside surface of the waveguide 5C. A TEFLON® with very high air content may be used to maximize the acoustic impedance difference between the filler material 10C and the waveguide outer surface. Note that the porous TEFLON® jacket also acts as a radial thermal insulator, so this may argue for a recirculating cooled filler material 10C. The waveguide 5C is enveloped with jacket 9A to prevent acoustic burning or energy leakage, wherein the jacket can be: (a) highly reflective to waves 11C; and (b) a poor transmitter of any ultrasound that may leak into the jacket 9A or otherwise leak to anything that contacts the waveguide 5C, such as a stray hand. In the waveguide 5C of FIG. 2C, the core may be any acoustically conductive material; for example, single strands or multiple strands of metal or glass. Useful metals include titanium alloys and super-elastic Nitinol alloys (available from NDC; Fremont, Calif.). Such fibers, wires or cables may be individually immersed or wrapped in a second medium that provides fiber/fiber acoustic isolation. For example, individual acoustics-carrying fibers could be wrapped with porous Teflon or other air-like material with good temperature resistance and lubricity and to possibly allow sliding of adjacent fibers to help improve waveguide flexibility and fatigue life. Overall cable flexibility can therefore be provided by a core 10C comprised of a bundle of metallic wires or glass fibers, preferably with air-like wrappers or nearby surroundings. Metallic fibers can pass heat along their length to the ends where it can be removed as by conduction or convection. Even with a metallic fiber waveguide one might embed a few additional optical fibers or electrical leads for power or data. These simply need to be inside the external jacketing somewhere.

The waveguide 5C may use an acoustic power sensor of the hydrophone type generally disclosed as 12A in FIG. 1. A transducer 3, 4 may be used that is also capable of area-wise parameter adjustments to negate the previously mentioned waveguide variations. The embodiment shown in FIG. 2C allows heat conduction transmission easily along its length and sufficiently enough out of the coated walls to maintain together safe operating temperatures. Presuming one uses a bundle of acoustically radially-isolated wires then acoustic phase-differences can be retained across them. Note that the TEFLON® coating, such as may be used as part of jacket 9A has a high temperature-resistance of greater than 200° C. The waveguides 5A and 5B of FIGS. 2A and 2B allow considerable heat transfer if the filler material 10A, 10B is a flowable filler material, and even moderate transfer even when the filler material is not flowed. We have emphasized TEFLON® as a preferred unwettable liner; however, we emphasize that any air-like water impermeable material such as many fluoropolymers may do the job. Other preferably porous air-like liner materials might be treated with hydrophobic coatings, at least on their interior surfaces, to act in a similar manner.

The filler material (as indicated in FIGS. 1, 2A-C (10A, 10B, 10BB, 10C) may be a flowable filler material that is forcibly flowed because flow establishes stable and non-chaotic laminar flowlines and radial temperature gradients. This will assure that the acoustic propagation paths along various paths in the waveguide will remain stable. Note that with area-wise phase control in transducer 3, 4, we can compensate for phase differences cause by different flow velocities as a function of radius. Solid wire bundle cores might even have some flow between them for cooling the bundle; however, in that case the flow does not carry significant, if any, acoustic power, but the wires do that instead.

Among other things, the invention contemplates using the ultrasound energy itself to cause such thermally-beneficial flow of flowable filler materials. This flow would be caused by the familiar acoustic streaming forces. An operator can electively compensate for flow-velocity differences across the waveguide cross-section or the system can automatically do that with area wise phase corrections using the area-wise multielement transducer 3, 4. Typically, if we are talking about a fluid propagation medium and not a wire bundle, a forced fluid velocity will be larger than any potential streaming velocity. Also, and beneficially, the forced or pumped fluid radial velocity symmetry will be more uniform even at bends in the waveguide.

FIG. 3 shows three additional embodiments of an applicator 6. The applicator 6 bridges the treatment acoustics from the delivery waveguide into the target tissue 8 via a tissue contacting or acoustically-coupling head (e.g., as shown as element 7 in FIG. 1) and ensures that the desired pattern of acoustics is applied, particularly if that pattern differs from that traveling in the waveguide under acceptable thermal circumstances. Note that the applicator will likely provide a more manipulation-friendly mechanism to apply the energy than the potentially unwieldy waveguide itself This is particularly true if the applicator steers or redirects acoustic energy as it exits the waveguide. Thus, the acoustic therapy applicator can serve a number of functions, including:

(1) redirecting acoustics in a useful direction, for example, redirecting the acoustic waves at a right angle to the waveguide and toward tissue;
(2) controllably focusing or defocusing acoustics, for example, focusing acoustics from the waveguide to a focus, beam, focal line or point within tissue;
(3) providing a disposable interface;
(4) providing an application-specific cooling arrangement; for example, the applicator can have structural heat sinks and circulated or emitted coolant;
(5) providing an application-specific bent or bendable (malleable) form; such applicators usually degrade after many bending cycles due to hot spots and require frequent replacement;
(6) providing for the sensor 12A of FIG. 1;
(7) providing a selection, kit or variety of applicators customized or optimized for particular therapies, patients, practitioners, body-parts, etc.; and/or
(8) employing the applicator to also co-mount other tools or sensors such as ultrasound imagers or surgical tools.

Figure 3A:
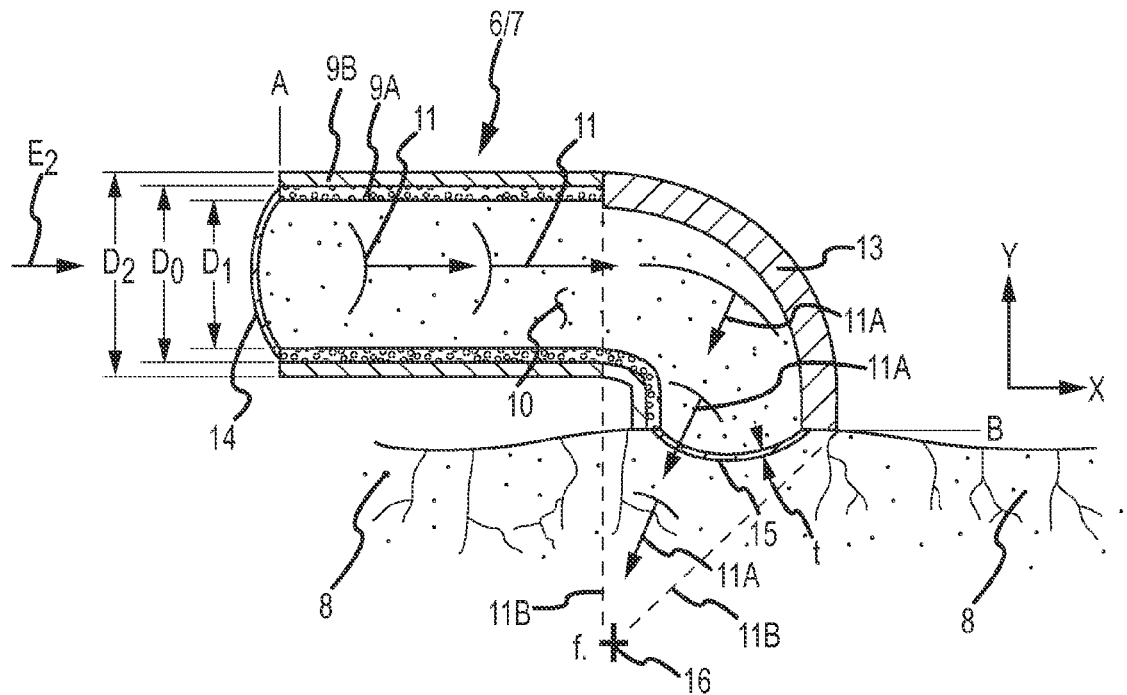

FIG. 3A shows an applicator 6 in contact with a target tissue 8. Note that no connected or coupled waveguide is shown, but would be included and connected to the applicator 6 (which would generally be to the left of the figures), from which acoustic energy $E_2$ exits and enters the applicator 6. Here, the ingoing mouth of the applicator is designated as plane A, and the outgoing port of the applicator as plane B. The applicator 6 of FIG. 3A is shown turning or redirecting the acoustic waves 11 into emanating acoustic waves 11A traveling to a focus spot 16 in the target tissue 8. The applicator 6 shown, for example, has a molded polymeric outer shell 9B, an inner acoustically reflective liner 9A (such as a porous expandable polymer material, such as TEFLON®) and a filler material 10 that is an acoustically conductive propagation liquid or other flowable material. Note that filler material 10 may be held within the applicator 6 by elastomeric diaphragms 14, 15. At the input mouth A is an elastomeric diaphragm 14. At the output port is a second elastomeric diaphragm 15. These have a thickness t. In effect the filler material 10 is encapsulated inside the applicator 6, but it slightly bulges out the elastomeric diaphragms 14, 15 as shown. In this embodiment, therefore, the waveguide filler material is in acoustic communication with the corresponding filler material of the applicator 10 by known gel or liquid-contact measures across or through the substantially acoustically-transparent membrane(s). For example, waveguide and applicator 6 of FIG. 3A may be both saline-filled, and have elastomeric diaphragms that cover their coupling corresponding ends. The membranes would co-wet each other if there are two together which mate face to face. In this case, such ends abut, using a water-like gel is just one example of known method of coupling acoustics. Moreover, the applicator can snap on, screw on or otherwise be attached to the waveguide in any manner. It will be noted in FIG. 3A that once the applicator 6 is mounted on the waveguide, then the elastomeric diaphragm 15 remains convex (as shown) to the target tissue 8. Thus diaphragm 15 may be water- or gel-coupled to target tissue 8 as well.

FIG. 3A shows an applicator 6 that also comprises an acoustic reflector 13. This reflector is different from material 9A or 9B. The reflector 13 may be an air-backed membrane or a solid-metal mirror. Its shape is configured to cause favorable beam focusing or to simply redirect the acoustic beam 11 without any focusing. Other examples of acoustic mirrors that may be used are widely known in the acoustics art.

Before proceeding to the next figure we wish to emphasize that we have taught liquid or gel filled waveguides as well as wire-bundle waveguides. It is within the inventive scope to utilize both in one system such as by using a wire-bundle waveguide and a liquid filled applicator. In that example the acoustics are emitted from the wire bundle upon entering the liquid medium of the applicator. Those familiar with acoustics will be aware that one may beneficially employ an acoustic matching layer(s) at this wire/liquid interface region to reduce acoustic reflections.

Figure 3B:
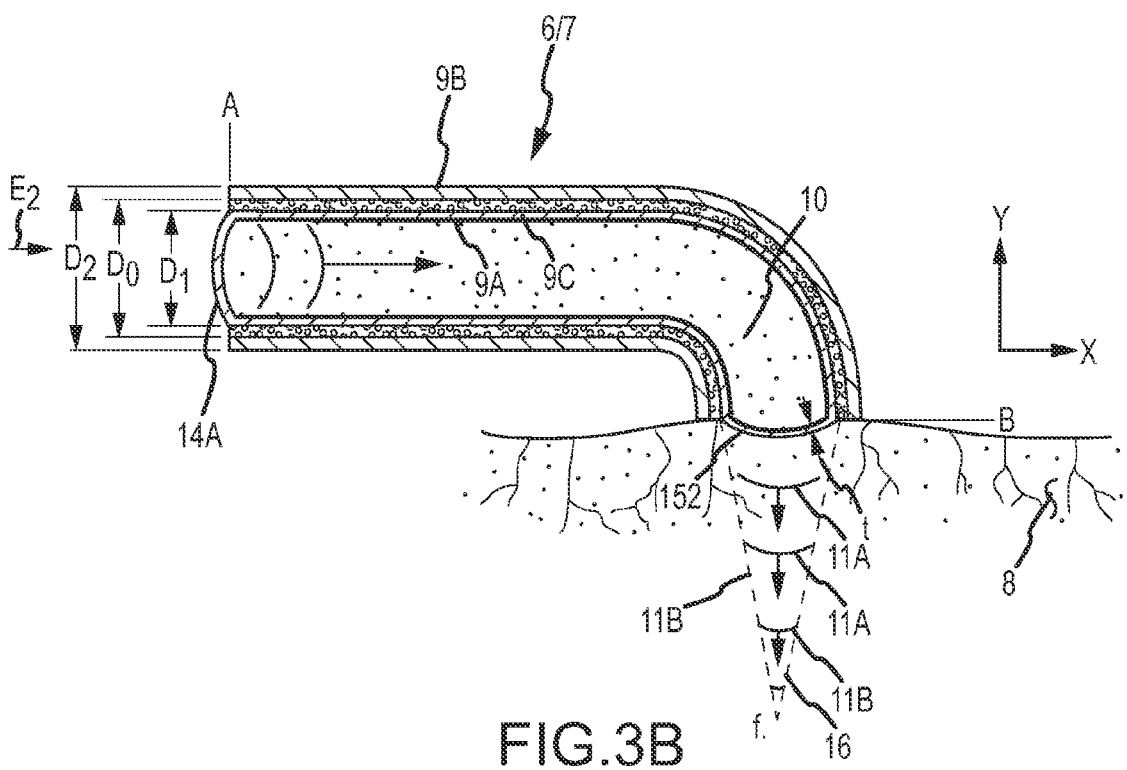

FIG. 3B shows an embodiment of an applicator 6 like that of FIG. 3A, but here, all or substantially all, of the entire applicator of FIG. 3B is lined with reflective liner material 9A. The elastomeric diaphragms 14A and 15A are now, instead, provided by a single, liquid-inflated balloon 9C placed inside the applicator. The balloon 9C has a thickness t. This applicator is shown focusing to a point 16 with emanating waves 11A. Although we are describing waveguides and applicators which contain propagation fluids even when disconnected or not in use, it is entirely within the inventive scope to drain propagation liquids from waveguides and/or applicators. Advantages of a drainage approach may include one or more of the following: a) the interiors of those parts may be cleaner or disinfected, b) one can eliminate some of the elastomeric membranes if fluid is not admitted until after the system/waveguide/applicator are connected to each other. We anticipate that most system will utilize an elastomeric or even rigid membrane at the applicator exit port adjacent tissue. This is so that the acoustic propagation medium is not admitted into the body, presuming that is a requirement.

FIG. 3C shows yet another embodiment of an applicator 6 of the invention. This applicator 6, instead of having a single liquid or flowable filler propagation material inside, has an array of individual sub-waveguides 10A-N, each propagating its own waves 11A-N. In one embodiment, each Nitinol (titanium-nickel) wire is separated or acoustically-isolated from its neighbor by a low-loss air-like material such as porous TEFLON®. An example of such a waveguide is shown in FIG. 3C and comprises a membrane 15B for skin contact. This membrane might be exchangeable and disposable. In this FIG. 3C embodiment, the individual wires 10A-N are likely different lengths, particularly in the region 16 behind the diaphragm 15B. Since the wires 10A-N are of different length, exiting acoustic waves arrive to the target tissue 8 at different times. Thus, once the acoustic energy has turned downward (e.g., as generally shown in FIG. 3C), the wire length may be set such that all wires have equal exit times. Alternatively, wire lengths may be provided and set to purposely cause focusing. The space 16, if any, may be filled with a filler medium that is flowable. In any event, wire-to-wire phase differences can be changed, corrected or favorably set to cause focusing when using a transducer 3, 4 that has area-wise distributed sub-elements which can be separately adjusted in phase and amplitude. Included in the scope is the wire bundle at the skin line or tissue interface having its bundle-end shaped for direct contact, comfort and/or focusing. Also included is the system being able to recognize a particular applicator and/or waveguide such that appropriate gross and/or fine presets for gross overall and/or sub-element phase and amplitude can be made.

The main points to be made by FIGS. 3A-3C are as follows:
(1) treatment acoustics may be redirected as desired, with or without focusing;
(2) the applicator may be made detachable and disposable;
(3) the applicator can incorporate an acoustic power sensor;
(4) the applicator can use one or both of homogenous propagation media or structured sub-waveguides;
(5) the applicator can incorporate tissue-cooling irrigation or tissue-illumination features;
(6) the applicator may be application-specific, malleable or provided as part of a kit comprising multiple different sizes, shapes or attributes;
(7) the applicator, like the waveguide 5 of FIG. 1, can also have flowed coolant or propagation media 10;
(8) for liquid based waveguides and/or applicators one might utilize a no-drainage or drainage strategy;
(9) one can mix and match a fluid based propagation approach with a wire-bundle based approach-and may incorporate acoustic matching layers in doing that;
(10) a particularly attractive embodiment has a wire-bundle based waveguide passing therapeutic acoustical energy into a liquid based applicator.

Focusing, if needed in scenario (10), could be done as by any one or more of a) area-wise phase delay control on a multielement transducer, b) a shaped focusing mirror anywhere in the acoustic path-such as in the applicator, c) a shaped mechanical acoustic lens anywhere in the path such as on or at the applicator/tissue interface region, d) purposeful length variation from wire to wire thereby introducing focusing phase delays. We mentioned earlier that an acoustic matching layer could beneficially be employed between the wire bundle waveguide and the liquid-filled applicator. It will be appreciated by acousticians that for the best performance and minimization of acoustic crosstalk one would arrange for each such waveguide subwire to have its own acoustically isolated matching layer segment.

While we have primarily taught round-section waveguides we include in the inventive scope other shapes-such as flat ribbon-type waveguides with at-least one highly flexible bending plane. While we have emphasized metallic wire and liquid/gel based waveguide propagation mediums one might instead utilize, for example, ceramic-metal mixtures such as "cermets." While we have taught wires being acoustic propagation paths we also emphasize that within the present scope is the use of wires for other known medical purposes-such as actuation pull wires on a robot or as electrical signal paths.

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A system for delivering therapeutic acoustic energy to a subject, comprising:
 a controller;
 at least one transducer operatively coupled to the controller and configured to emit therapeutic acoustic energy;
 an acoustic waveguide comprising an input port coupleable to the transducer and an exit port;
 an acoustic energy applicator acoustically coupled to the exit port of the waveguide, said applicator also acoustically coupleable with said subject, wherein said applicator is configured to direct the acoustic energy in a direction different than a direction of the exit port of the waveguide; and
 at least one acoustic energy detection sensor operably connected to the transducer and positioned at, in, or near the applicator or waveguide exit port,
 wherein acoustic energy emitted by the transducer passes through the waveguide and impinges on the acoustic detection sensor before exiting the applicator, and the acoustic detection sensor is configured to detect the delivered acoustic energy and provide feedback to the controller,
 wherein the controller is configured to adjust the emission of acoustic energy by the transducer responsive to the feedback so that power of the acoustic energy at the exit port of the waveguide is substantially equal to a select or predetermined power.

2. The system of claim 1, wherein the feedback permits a user of the system to perform one or more of:
 assessing acoustic energy being delivered, or about to be delivered, to a subject;
 assessing acoustic energy loss in the waveguide, in the input port, in the exit port, or in the applicator;
 adjusting an operational parameter of the transducer to modify acoustic energy being delivered or which is deliverable to or through the applicator; or
 correcting phase-error or amplitude to one or more sub-elements of the transducer, wherein the transducer has multiple sub-elements.

3. The system of claim 1 wherein the controller is configured to adjust emission of acoustic energy to prevent one or more of:
 a loss of therapeutic benefit,
 an undesired lack of uniformity in a therapeutic benefit;
 an undesired extent or lack of extent of a therapeutic benefit at at least one location;
 undesirable phase errors or differences; or
 undesirable amplitude errors or differences.

4. The system of claim 1 wherein the acoustic detection sensor is one or more of:
 mounted on, or in, the waveguide itself;
 mounted on or in the acoustic energy applicator;
 mounted in an acoustic path for energy being delivered by the system; and
 mounted on or in target tissue.

5. The system of claim 1, further comprising a filler material that serves as an acoustic propagation medium, wherein the filler material is at least partially enclosed inside the waveguide.

6. The system of claim 5, wherein the filler material is a liquid, gel, paste, cream, emulsion, water or aqueous solution, flowable or flowed material or combinations thereof.

7. The system of claim 5, wherein the filler material is aqueous or is saline.

8. The system of claim 5, wherein the filler material includes at least one metallic, glass, ceramic or metal-ceramic member, fiber, wire, or cable that runs along the length of the waveguide and along which acoustic energy propagates.

9. The system of claim 5, wherein the filler material includes a plurality of metallic, glass, ceramic, or ceramic-metal members, fibers, wires, or cables that each run along the length of the waveguide and along which acoustic energy propagates, and wherein each member, fiber, wire or cable is substantially acoustically isolated from an adjacent member, fiber, wire or cable.

10. The system of claim 1, wherein the waveguide further comprises a wall material that is one or more of: porous, permeable, acoustically reflective, fully gaseous, partly gaseous, fully vapor-containing, partly vapor-containing, fully air-saturated, partly air-saturated, fully air-infiltrated, and partly air-infiltrated.

11. The system of claim 1, further comprising a filler material that is at least partially enclosed inside the waveguide, the filler material serving as an acoustic propagation medium, wherein the waveguide comprises a wall material, and wherein the filler material does not substantially infiltrate the wall material during acoustic power propagation along the waveguide, the wall material acting to at least radially reflect and contain acoustical energy propagating within the filler material.

12. The system of claim 9, wherein the waveguide includes a porous or permeable wall material that is partially filled with air or vapor.

13. The system of claim 1, wherein the waveguide comprises a substantially unwettable wall material, and further comprising a filler material contained by the substantially unwettable wall material.

14. The system of claim 11, further comprising a vacuum coupled to the propagation medium to de-gas the propagation medium.

15. The system of claim 1, wherein the transducer includes a face that emits into the waveguide and allows for at least one of phase delay or intensity control across the face.

16. The system of claim 1, wherein the transducer comprises a plurality of sub-elements and wherein the transducer is configured for variation between each of the plurality of sub-elements in at least one operational acoustic parameter, and the variation, at least in part, is used to correct for a degradation or distortion of the acoustic energy in the waveguide or to form an acoustic energy beam or pattern.

17. The system of claim 16, wherein an operational parameter of the transducer is varied or of different value between at least two of the transducer's sub-elements.

18. The system of claim 17, wherein the varied or different value parameter is any of amplitude, phase, frequency, or excitation waveform.

19. The system of claim 16, wherein the variation is provided based in part from feedback from at least one acoustic detection sensor and, at least in part, corrects or adjusts for an acoustic degradation or distortion.

20. The system of claim 5 wherein the filler material comprises at least one selected from the group consisting of:

a convected or pumped heat-transfer medium, the convection being forced or natural;
a circulated medium;
a degassed medium;
a medium recirculated within or along the waveguide, and
a medium contained by one or more membrane-like members that are configured to pass acoustical energy.

21. A system for delivering therapeutic acoustic energy to a subject, comprising:
a controller;
an acoustic transducer operatively coupled to the controller;
a flexible acoustic waveguide, the waveguide including an input port, an exit port, and an acoustic detection sensor operably connected to the acoustic transducer; and
an acoustic energy applicator connected to the waveguide, wherein acoustic energy emitted by the transducer passes through the waveguide; and
wherein the acoustic detection sensor is situated near the exit port of the waveguide or applicator and is configured to detect the acoustic energy as the acoustic energy propagates from the waveguide or applicator to the subject and provide feedback regarding the acoustic energy to the controller and the controller is configured to compensate for detected degradation, distortion or non-optimal state in the acoustic energy supplied to the applicator responsive to the feedback.

22. The system of claim 1, wherein said applicator is configured to direct the acoustic energy in a direction different than a direction of the exit port of the waveguide.

23. The system of claim 22, wherein a portion of said acoustic waveguide including the exit port extends along an axis, and wherein at least a portion of said applicator is configured to be bendable so as to allow the portion of said applicator to extend at a transverse angle relative to the axis.

24. The system of claim 21, wherein the controller is configured to perform at least one function selected from the group consisting of:
adjusting one or more emitter powers or operational parameters of at least one emitter portion in order to negate waveguide output power variation;
adjusting one or more emitter phases among segments of a multisegment transducer to preserve or obtain a desired phase pattern
adjusting treatment time to negate effects of variation in waveguide output power; and
adjusting a treatment dose parameter to negate effects of variation in waveguide output power.

25. The system of claim 21, further comprising a filler material that actively or passively cools the waveguide, wherein the filler material is at least partially enclosed inside the waveguide.

26. The system of claim 25, wherein the filler material is flowable and actively cools the waveguide, said filler material being circulated through at least the waveguide at least once.

27. The system of claim 21, wherein the energy applicator attached to the waveguide further comprises at least one selected from the group consisting of:
a coupling gel or coupling flowable material in an interface between the applicator and the waveguide;
an applicator propagation medium that is flowed; and
a connection to the waveguide through which the acoustic medium flows in the energy applicator.

28. The system of claim 21, wherein the applicator comprises at least one selected from the group consisting of:
a flexible diaphragm through which the acoustic energy flows;

a porous wall liner;
a permeable wall liner;
an acoustically reflective lens;
an acoustically reflective mirror; and
an illuminator.

29. A system for delivering therapeutic acoustic energy to a subject, comprising:
   a controller;
   a multisegment or multielement acoustic transducer operatively coupled to the controller and comprising a plurality of sub-elements, the acoustic transducer capable of variation between each of the plurality of sub-elements in at least one operational acoustic parameter;
   a flexible acoustic waveguide comprising an input port and an exit port;
   an acoustic energy applicator acoustically coupled to the exit port of the waveguide;
   an acoustic detection sensor situated at or near the waveguide exit port or applicator and being operably connected to the acoustic transducer; and
   a filler material that provides cooling for the waveguide;
   wherein emitted acoustic energy passes through the waveguide to the applicator and impinges on the sensor before exiting the applicator, and
   wherein the acoustic detection sensor is configured to detect the acoustic energy and provide feedback regarding the acoustic energy to the controller, wherein the controller is configured to change at least one transducer segment operational parameter to maintain a delivered or deliverable power or power uniformity if the feedback indicates that the exit power or power uniformity is different from the desired delivered or deliverable power or power uniformity.

30. A device for delivering acoustic energy to a subject, comprising:
   a controller;
   an acoustic waveguide comprising an input port and an exit port,
   an acoustic detection component configured to be operably connected to a transducer configured to deliver acoustic energy, wherein the acoustic detection component is configured to detect the delivered acoustic energy as the acoustic energy propagates from the waveguide to the subject near the exit port of the acoustic waveguide and provide feedback to the controller, wherein the controller is configured to adjust delivery of acoustic energy responsive to the feedback so that power of the adjusted acoustic energy at the exit port of the waveguide is substantially equal to a select or predetermined power; and
   an acoustic energy applicator connected to the waveguide.

31. The device of claim 30, wherein the waveguide is re-usable.

32. A method of delivering a predetermined dose or pattern of acoustic energy to a subject, comprising:
   providing a transducer configured to produce acoustic energy and a controller configured to adjust an operational parameter of the transducer;
   operably connecting the transducer to an acoustic waveguide comprising an input port and an exit port;
   providing an acoustic energy applicator operably connected to the waveguide;
   providing an acoustic energy detection sensor situated at or near the waveguide exit port or applicator;
   providing power to the transducer to emit the acoustic energy in a pre-selected amount or energy pattern through the waveguide, through the exit port and the applicator; and
   monitoring the acoustic detection sensor, wherein said acoustic detection sensor detects the acoustic energy as the acoustic energy propagates from the waveguide or applicator to the subject and provides feedback regarding the acoustic energy to the controller, and the controller is configured to adjust the operational parameter of the transducer to compensate for detected degradation or distortion in the acoustic energy supplied to the applicator, responsive to the feedback, to maintain or achieve a selected exit port power or pattern.

* * * * *